United States Patent [19]

Gencarelli et al.

[11] Patent Number: 4,593,105

[45] Date of Patent: Jun. 3, 1986

[54] PROCESS FOR MAKING 2-MERCAPTO BENZIMIDAZOLES IN THE PRESENCE OF A WATER-INSOLUBLE ALKANOL

[75] Inventors: Richard A. Gencarelli, Waterbury; Edward L. Wheeler, Watertown, both of Conn.

[73] Assignee: Uniroyal Chemical Company, Inc., Middlebury, Conn.

[21] Appl. No.: 413,921

[22] Filed: Sep. 1, 1982

Related U.S. Application Data

[63] Continuation-in-part of Ser. No. 259,732, May 1, 1981, abandoned.

[51] Int. Cl.$^4$ ............................................. C07D 235/28
[52] U.S. Cl. ..................................... 548/329; 548/305
[58] Field of Search ................................ 548/329, 305

[56] References Cited

FOREIGN PATENT DOCUMENTS 2214600  10/1973  Fed. Rep. of Germany ...... 548/329

OTHER PUBLICATIONS

Allen, J. A. et al., Organic Synthesis, vol. 4, 569–570, 1963.

*Primary Examiner*—George F. Lesmes
*Assistant Examiner*—S. A. Gibson
*Attorney, Agent, or Firm*—John A. Shedden; William E. Dickheiser

[57] ABSTRACT

A process is provided for making benzimidazoles having the formula

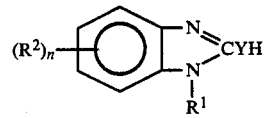

wherein Y is oxygen, sulfur or —NH; $R^1$ is hydrogen, $C_1$–$C_{12}$ alkyl, $C_5$–$C_6$ cycloalkyl, $C_6$–$C_{10}$ aryl, $C_7$–$C_9$ aralkyl or $C_7$–$C_9$ alkaryl; $R^2$ is hydrogen, $C_1$–$C_4$ alkyl, $C_1$–$C_4$ alkoxy or halogen; and n is 1 or 2; comprising reacting a compound having the formula ZYCN, wherein Z is an alkali metal or ammonium moiety and Y has the meanings above; with a compound having the formula

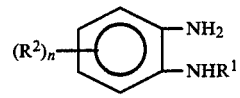

wherein $R^1$, $R^2$ and n have the meanings above, in the presence of a $C_4$–$C_{10}$ alkanol and, except when Z is $NH_4$, in the presence of an acid.

5 Claims, No Drawings

PROCESS FOR MAKING 2-MERCAPTO BENZIMIDAZOLES IN THE PRESENCE OF A WATER-INSOLUBLE ALKANOL

This application is a continuation-in-part of application Ser. No. 259,732 filed May 1, 1981, now abandoned.

This invention relates to a method for making 5-membered ring compounds containing N and C atoms by reacting certain (thio)cyanate salts or cyanamide salts with aromatic compounds having $NH_2$ functionality vicinal to an amine group, in the presence of an acid except where said cyanate, thiocyanate or cyanamide is an ammonium salt.

The following references are of interest:

Org. Syn. Col. Vol. IV, p. 180 which discloses a process for preparing a thiourea from an amine HCl and ammonium thiocyanate.

U.S. Pat. No. 3,455,948, Stedman, July 15, 1969, particularly the preparation of a thiourea in Example 7.

EPO 0-005-276, Nov. 14, 1979, Hoechst AG, describing preparation of a thiourea.

Heterocyclic Compounds, Vol. 5, Elderfield, p. 285, disclosing preparation of 2-mercaptobenzimidazoles, etc.

Thiourea, D. C. Schroeder, Chem. Rev. Vol. 55, pp. 181-228, which contains a review of thiourea chemistry.

EPO 0-012-933, July 9, 1980, Hoechst AG, disclosing production of amino-benzimidazolone.

Allen et al, Organic Syntheses 4, p. 569-570 (1963) discloses a method for making 2-mercaptobenzimidazole by reacting first o-phenylenediamine with potassium ethyl xanthate in an ethanol-water mixture while removing hydrogen sulfide, then treating the resultant potassium salt with acetic acid; furthermore there is mentioned the reaction of o-phenylenediamine with aqueous potassium thiocyanate. Nowhere is there any indiction of the use of higher, i.e., $C_4$-$C_{10}$ alkanol of this invention as solvent and of the much higher product yields achieved with such alkanols.

Allen et al, Organic Syntheses, 3, p. 76-78 (1955) teaches the preparation of 2-amino-6-methyl-benzothiazole from the p-tolylthiourea precursor and sulfuryl chloride.

Fieser et al, Reagents for Organic Synthesis, p. 1105-1106 (1967) also deals with 2-amino-6-methyl-benzothiazole from p-tolylthiourea and sulfuryl chloride and subsequent treatment with caustic.

Likhosherstov et al, Chem. Abstracts, 28, 2690 (1934) discloses preparation of certain substituted 4- or 6-thiocyano-2-aminobenzothiazoles from various mono- or di-thiocyanoaminobenzenes.

Mel'nikov et al, Chem. Abstracts 39, 934 (1945), deals with an electrochemical method for making substituted 2-aminobenzothiazoles from e.g. toluidine and ammonium thiocyanate.

The instant process provides benzimidazole products having improved purity and color at high yields.

In one aspect the invention is concerned with a one-step process for the preparation of such compounds as 2-hydroxy, 2-amino or 2-mercaptobenzimidazoles by reacting such materials as o-phenylenediamines or the like with an inorganic cyanate, thiocyanate or cyanamide. An acid is used with the cyanate, thiocyanate or cyanamide in those cases where the anion is not the ammonium ion.

The reaction is run in a $C_4$-$C_{10}$ alkanol as solvent which enables removal of impurities and color by extracting the product into aqueous sodium hydroxide as its sodium salt, and then precipitating the product from the aqueous phase with acid.

In accordance with the present state of the prior art 2-mercaptobenzimidazole is prepared by reacting o-phenylenediamines with carbon disulfide. This reaction generates one mole of highly toxic hydrogen sulfide per mole of product and this hydrogen sulfide must be disposed of. In the process of this invention only a trace of hydrogen sulfide is formed, while the major by-product is ammonia.

The invention may accordingly be characterized as a process for making a 5-membered heterocyclic compound having the structural formula

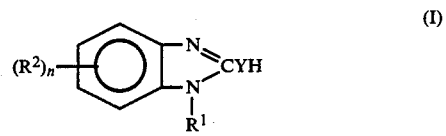
(I)

wherein n is 1 or 2; Y is oxygen, NH or sulfur; $R^1$ is hydrogen, $C_1$-$C_{12}$ alkyl, $C_5$-$C_6$ cycloalkyl, $C_6$-$C_{10}$ aryl, $C_7$-$C_9$ alkaryl or $C_7$-$C_9$ aralkyl; $R^2$ is hydrogen $C_1$-$C_4$ alkyl, $C_1$-$C_4$ alkoxy or halogen such as chlorine and bromine; comprising reacting a compound having the structural formula, ZYCN, wherein Z is an alkali metal or ammonium moiety, and Y is as defined above, with a compound having the structural formula

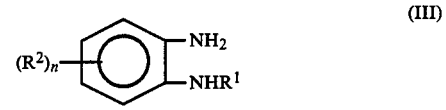
(III)

wherein n, $R^1$, and $R^2$ have the meanings above; in the presence of a $C_4$-$C_{10}$ alkanol and, except when Z is $NH_4$, in the presence of an acid. It will be understood that if n equals 2, the $R^2$ groups may be the same or different.

The process of the invention is of particular interest as allowing production of such useful compounds as antioxidants (e.g., 2-mercapto-benzimidazole) at high yields and purity, at low cost and essentially without hydrogen sulfide by-product.

One preferred practice of the invention may be outlined as follows:

To a suitable reaction vessel equipped with agitation and temperature determining means, as well as with condensing means, are added the $C_4$-$C_{10}$ alcohol, the ZYCN compound (e.g. ammonium or alkali metal cyanate, thiocyanate or cyanamide) and the vicinally functional compound (e.g., o-arylenediamine) at essentially stoichiometric amounts. If the ZYCN compound is not an ammonium salt, an about equimolar (to the (thio)cyanate or cyanamide compound) amount of acid (usually mineral acid such as HCl, $H_2SO_4$, etc.) is charged, and, while agitating, the reaction mixture is heated to about 115°-200° C. for about 2 to 8 hours. After completion of the reaction, the reaction mixture is treated with aqueous caustic. The aqueous layer is separated and it is neutralized with acid. The precipitate (product) is removed by filtration.

In many cases the preferred solvent for the reaction is a $C_6$-$C_{10}$ alkanol, most preferably a $C_6$-$C_8$ alkanol. The concentration of reactants in the solvent is usually within the range of about 200 or less to about 900 or more g/l, preferably about 400 to about 700, more preferably about 600. Reaction temperatures are ordinarily within the range of about 110° to about 200° C. or more, depending on the particular reactants, preferably about 140° to about 180° C., more preferably from about 140° to about 160°. Reaction carried out for about 2 hours or less to about 12 hours or more, preferably about 4 to about 8 hours, more preferably about 6 hours at any desired pressure, usually atmospheric, although subatmospheric or superatmospheric pressure (e.g. 10 atmospheres or more) may be used if desired.

Valuable products which may be prepared by the method of the invention include but are not limited to
2-mercapto-N,4,5-trimethylimidazole
1-hexyl-2-mercapto-4-propylimidazole
1-hexyl-2-mercapto-5-propylimidazole
1-cyclohexyl-4-hexyl-2-mercaptoimidazole
1-cyclohexyl-5-hexyl-2-mercaptoimidazole
2-hydroxy-1,4,5-triphenylimidazole
1-benzyl-2-hydroxy-4-tolylimidazole
1-benzyl-2-hydroxy-5-tolylimidazole
2-mercapto-1-(phenylpropyl)imidazole
2-aminobenzimidazole
2-amino-5-methoxybenzimidazole
2-hydroxy-5,6-dichlorobenzimidazole
2-mercapto-6-bromobenzimidazole
5-chloro-2-mercapto-6-methoxybenzimidazole
5-t-butoxy-2-aminobenzimidazole
1-dodecyl-2-mercaptobenzimidazole
1-octyl-2-hydroxybenzimidazole
2-amino-N-benzylbenzimidazole
2-mercapto-1-phenylbenzimidazole
2-hydroxy-5-propoxybenzimidazole
5-bromo-6-chloro-2-mercaptobenzimidazole In one preferred practice of the invention the solvent is selected from $C_6$–$C_{10}$ alkanol, the reaction temperature is from 140° to 180° C. and the reaction time is from 4 to 8 hours. Particularly preferred solvents are $C_6$–$C_8$ alkanols such as hexanol and 2-ethylhexanol.

Of particular interest is a process including the following product purification steps:
(a) Extraction of product from the organic phase with aqueous caustic;
(b) Neutralizing the caustic solution from (a) with acid;
(c) Isolating the product from step (b) by filtration.

Preferably, prior to step (b), the mixture of product in hot aqueous caustic is treated with charcoal in order to remove impurities.

The following examples will serve to illustrate the practice of the invention in more detail.

EXAMPLE 1

Preparation of 2-Mercapto-4(5)-methylbenzimidazole

To a one liter round-bottom, three-necked flask equipped with an agitator, a thermometer, a reflux condenser and a Stark and Dean trap were added 122 g (1.0 mole) ortho-toluenediamine (mixture of 34% 2,3-toluenediamine, 63% 3,4-toluenediamine, 2% other isomers and 1% water), 244 g 2-ethylhexanol and 145.2 g 50% aqueous ammonium thiocyanate. The mixture was heated to reflux (ca. 164° C.), and the water was azeotroped out for about one hour. The reaction mixture was kept at 164° C. for 6 hours. The mixture was cooled to about 100° C., and 41 g of solid sodium hydroxide in 500 ml of water was added while stirring. The mixture was transferred to a separating funnel, and the aqueous layer was removed. The alcohol layer was washed with 500 ml of water, and the water drawn off. The combined water layers were neutralized with acid and the title product was removed by filtration and dried.

EXAMPLE 2

Preparation of 2-Mercapto-4(5)-methylbenzimidazole

To a two-liter, three-necked round bottom flask equipped with a thermometer, agitator, dropping funnel and a Stark and Dean trap with condenser were added 122 g (1.0 mol) o-toluenediamine, 81 g (1.0 mol) sodium thiocyanate and 500 ml n-hexanol. While stirring, 84 ml concentrated hydrochloric acid was added, and the mixture was then heated to 160° C. The water present was azeotroped out of the flask during said heating period (ca. 1 hour). The mixture was refluxed (ca. 160° C.) for five hours and then no further heat was applied. 170 ml of 6N sodium hydroxide (diluted to 250 ml) was slowly added to the reaction mixture which continued to reflux. After cooling the aqueous layer was removed and neutralized. A small amount (ca. 8 g) of a white solid was isolated by filtration. The hexanol portion was treated with about two liters of water. This aqueous portion was acidified causing a white solid product to precipitate. The product was isolated by filtration and dried. Total product yield was 159.5 g (97.3% of theory).

EXAMPLES 3–16

Following essentially the procedures of Examples 1 and 2 respectively, additional preparations were undertaken using various reactants, solvents and process conditions, all summarized in Table I. In examples 3–11 the product is 2-mercapto-4(5)-methylbenzimidazole. In Example 12 the product is 2-mercaptobenzimidazole.

The results demonstrate the usefulness of the process of this invention for the preparation of 5-membered heterocyclic chemicals in an easy and efficient manner.

EXAMPLE 13

(Comparison)

To a 2-liter Hastalloy (trademark) autoclave were added 122 g o-toluenediamine, 76 g ammonium thiocyanate and 600 ml water. The mixture was heated at 150° C. for 8 hours (pressure ca. 570 kPa), after which time it was washed with ca. 300 ml methanol. The methanol was then removed from the mixture by distillation. To the remaining portion of that mixture was added 170 ml sodium hydroxide (6N), and the total volume of the mixture was increased to two liters by the addition of water. The resultant mixture was shaken with 150 ml hexanol. The water layer was removed from the mixture and neutralized with sulfuric acid (6N) which caused precipitation of the product, 2-mercapto-4(5)-methylbenzimidazole. The product was filtered out and dried. Yield: 67 g (41%). It is noted that the use of water as solvent results in low yield of product.

EXAMPLE 14

Preparation of 2-Aminobenzimidazole

Using the same equipment as described in Example 1, 183 g 2-ethylhexanol, 122 g o-toluenediamine, 64 g sodium cyanamide and 84.3 ml concentrated HCl were placed into the reactor. While heating the mixtures to 164° C. the water was azeotroped off, and then the reaction mixture was kept at 164° C. for 5 hours. The mixture was cooled to room temperature. The title product was extracted from the solvent with aqueous acid followed by neutralization which caused crystallization of the product. The product was isolated by filtration.

TABLE I

|  | Example | | | | |
|---|---|---|---|---|---|
|  | 3* | 4 | 5 | 6 | 9* |
| TDA[1], mol | 1 | 1 | 1 | 1 | 1 |
| PDA[2], mol | — | — | — | — | — |
| XSCN, mole | 1 | 1 | 1 | 1 | 1 |
| X of XSCN | K | Na | Na | Na | Na |
| Acid: HCl, mol | 1 | — | 1 | 1 | — |
| Acid: $H_2SO_4$, mol | — | 1 | — | — | 1 |
| Solvent | $H_2O$ | hexanol | xylene | hexanol | NBU[4] |
| Solvent, ml | 400 | 150 | 500 | 220 | 500 |
| Reaction temp., °C. | 150 | 147 | 135 | 162 | 115 |
| Reaction time, hrs. | 6 | 19 | 4 | 5.5 | 8 |
| Yield, g | 83 | 150 | 125 | 162 | 106 |
| Yield, %[5] | 51 | 92 | 76 | 99 | 65 |

|  | Example | | | | |
|---|---|---|---|---|---|
|  | 8 | 9 | 10 | 11 | 12 |
| TDA[1], mol | 1 | 1 | 1 | 1 | — |
| PDA[2], mol | — | — | — | — | 1 |
| XSCN, mole | 1 | 1 | 1 | 1 | 1 |
| X of XSCN | $NH_4$ | $NH_4$ | $NH_4$ | $NH_4$ | $NH_4$ |
| Acid: HCl, mol | — | — | — | — | — |
| Acid: $H_2SO_4$, mol | — | — | — | — | — |
| Solvent | 2EH[3] | NBU | hexanol | decanol | 2EH |
| Solvent, ml | 222 | 400 | 220 | 170 | 220 |
| Reaction temp., °C. | 164 | 117 | 160 | 164 | 164 |
| Reaction time, hrs. | 6 | 7 | 6 | 6 | 5 |
| Yield, g | 152 | 123 | 152 | 130 | 128 |
| Yield, %[5] | 93 | 75 | 93 | 79 | 85 |

Remarks:
[1] o-toluenediamine
[2] o-phenylenediamine
[3] 2-ethylhexanol
[4] n-butanol
[5] % of theoretical yield based on appropriate [1] through [5]
*outside the invention

We claim:

1. A process for making a benzimidazole having the formula:

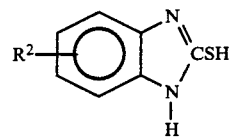

wherein $R^2$ is hydrogen or methyl comprising:
(a) reacting a compound having the formula ZSCN, wherein Z is Na, K or $NH_4$, with a compound having the formula:

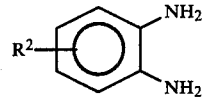

wherein $R^2$ has the meanings above, in the presence of a n-hexanol or 2-ethylhexanol alcohol, and, except when Z is $NH_4$, in the presence of an acid;
(b) azeotropically removing the water from the reaction mixture;
(c) extracting the benzimidazole from the alcohol with aqueous caustic;
(d) neutralizing the reaction mixture (c) with acid; and
(e) isolating the imidazole from the neutralized reaction mixture.

2. The process of claim 1 wherein the reaction temperature is from 117° to 200° C.

3. The process of claim 1 wherein Z is sodium, potassium or ammonium.

4. The process of claim 1 wherein said alkanol is hexanol, or 2-ethyl-hexanol and said acid is hydrochloric acid or sulfuric acid.

5. The process of claim 1 wherein said alkanol is hexanol or 2-ethylhexanol and the reaction temperature is from 147° to 164° C.

* * * * *